United States Patent
Feuerlein et al.

(10) Patent No.: US 10,825,208 B2
(45) Date of Patent: Nov. 3, 2020

(54) ADAPTIVE METHOD FOR GENERATING ARTIFACT-REDUCED CT IMAGE DATA

(71) Applicant: Siemens Healthcare GmbH, Erlangen (DE)

(72) Inventors: Ute Feuerlein, Erlangen (DE);
Christian Hofmann, Erlangen (DE);
Robert Mayer, Lauf/Schoenberg (DE);
Rainer Raupach, Heroldsbach (DE);
Grzegorz Soza, Heroldsberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 205 days.

(21) Appl. No.: 15/963,392

(22) Filed: Apr. 26, 2018

(65) Prior Publication Data

US 2018/0322664 A1 Nov. 8, 2018

(30) Foreign Application Priority Data

May 3, 2017 (EP) .................................... 17169269

(51) Int. Cl.
*G06T 11/00* (2006.01)
*A61B 6/00* (2006.01)
(Continued)

(52) U.S. Cl.
CPC .......... *G06T 11/003* (2013.01); *A61B 6/5258* (2013.01); *G06T 7/0012* (2013.01);
(Continued)

(58) Field of Classification Search
CPC ..... A61B 6/032; A61B 6/5258; G06T 11/003; G06T 11/008; G06T 2207/10081; G06T 7/0012
See application file for complete search history.

(56) References Cited

U.S. PATENT DOCUMENTS

| | | |
|---|---|---|
| 2016/0136458 A1 | 5/2016 | Taguchi et al. |
| 2017/0270687 A1 | 9/2017 | Manhart |
| 2019/0188885 A1* | 6/2019 | Grass .................... G06T 3/0068 |

FOREIGN PATENT DOCUMENTS

| | | |
|---|---|---|
| DE | 102015014908 A1 | 5/2016 |
| EP | 2998729 A1 | 3/2016 |
| EP | 3219260 A1 | 9/2017 |

OTHER PUBLICATIONS

Extended European Search Report dated Apr. 30, 2018.

\* cited by examiner

*Primary Examiner* — Nirav G Patel
(74) *Attorney, Agent, or Firm* — Harness, Dickey & Pierce, P.L.C.

(57) ABSTRACT

An adaptive method for generating CT image data is described. In the method, projection measurement data of an examination region of an examination object is acquired. Furthermore, uncorrected image data of the examination region is generated. Artifact-affected subregions of the examination region are determined on the basis of at least one part of the uncorrected image data. An artifact-reduced image reconstruction is carried out in the artifact-affected subregions of the examination region. Only artifact-reduced subimage data of the artifact-affected subregions is generated. Finally, artifact-reduced image data of the entire examination region is generated by combining at least one part of the uncorrected image data and the artifact-reduced subimage data. A reconstruction device is also described. Moreover, a computed tomography system is described.

22 Claims, 5 Drawing Sheets

(51) Int. Cl.
 *G06T 7/00* (2017.01)
 *A61B 6/03* (2006.01)
(52) U.S. Cl.
 CPC ............. *G06T 11/008* (2013.01); *A61B 6/032* (2013.01); *G06T 2207/10081* (2013.01)

ADAPTIVE METHOD FOR GENERATING ARTIFACT-REDUCED CT IMAGE DATA

PRIORITY STATEMENT

The present application hereby claims priority under 35 U.S.C. § 119 to European patent application number EP17169269.2 filed May 3, 2017, the entire contents of which are hereby incorporated herein by reference.

FIELD

At least one embodiment of the invention generally relates to an adaptive method for generating CT image data. Moreover, at least one embodiment of the invention generally relates to an image data reconstruction device. Furthermore, at least one embodiment of the invention generally relates to a computed tomography system.

BACKGROUND

One imaging method that is used frequently in medicine is computed tomography (CT). Computed tomography is based upon the capture of x-ray radiation, wherein what is known as projection measurement data is generated. In CT systems, a combination of an x-ray source and, mounted opposite thereto, an x-ray detector, said combination being arranged on a gantry, typically revolves round a scanning space in which the examination object (which is identified below as a patient, but without restricting the generality) is situated. The center of rotation (also known as "isocenter") coincides here with what is known as a system axis z. During one or more rotations, the patient is irradiated with x-ray radiation from the x-ray source, wherein projection measurement data or x-ray projection data is captured with the aid of the x-ray detector positioned opposite thereto. Image data, which is displayed to the user for assessment, is then reconstructed on the basis of the projection measurement data.

The projection measurement data generated is dependent, in particular, on the construction of the x-ray detector. X-ray detectors typically have a plurality of detection units which are usually arranged in the form of a regular pixel array. The detection units each generate a detection signal for x-ray radiation incident on the detection units, which signal is analyzed at particular time points with regard to intensity and spectral distribution of the x-ray radiation in order to draw conclusions regarding the examination object and to generate projection measurement data.

With the reconstruction of image data on the basis of the projection measurement data, artifacts, in particular metal artifacts, frequently occur. These interferences are generally caused by implants or prostheses in the body of the examined patient. For instance, with a skull x-ray dental implants may result in artifacts even if they themselves lie outside of the actual recording region, for instance the region of the brain.

In order to reduce artifacts in the image representation, special reconstructions can be carried out. It is often only after an image recording and a visual inspection of the image data reconstructed in the process that an artifact-reduced reconstruction is determined to be necessary. To this end, the image data records generated must firstly be visually inspected and then a decision is made to determine whether or not an additional artifact-reduced reconstruction is useful. The user must then request such an additional artifact-reduced reconstruction. As a result of the additional reconstruction, the entire data volume and the required outlay of time are significantly increased.

SUMMARY

The inventors have recognized that here is a problem of generating high quality image data with as low an outlay as possible in terms of time and computer effort.

At least one embodiment is directed to an adaptive method for generating CT image data; at least one embodiment is directed to an image data reconstruction device and at least one embodiment is directed to a computed tomography system.

With at least one embodiment of the inventive adaptive method for generating CT image data, projection measurement data is acquired of an examination region of an examination object. Furthermore, uncorrected image data is generated of the examination region. The examination region may be a body region of a patient, for instance. In the event of a non-medical application, the examination region may however also be part of an inanimate object. The uncorrected image data can be reconstructed for instance on the basis of the projection measurement data, it can however also comprise image data, which is obtained by recording a topogram or by generating RTD data (Real-time Display Data), i.e. real-time image data, sometimes also referred to as raw image data. In general image data of the examination region is to be understood as "uncorrected" image data, which has not yet been subjected to artifact correction and may have image artifacts, for instance metal artifacts.

At least one embodiment of the inventive image data reconstruction device has an input interface for acquiring projection measurement data of an examination region of an examination object. Part of the inventive image data reconstruction device is also a reconstruction unit for reconstructing uncorrected image data on the basis of the projection measurement data. At least one embodiment of the inventive image data reconstruction device moreover comprises a subregion determination unit for determining artifact-affected subregions of the examination region on the basis of uncorrected image data. Furthermore, at least one embodiment of the inventive image data reconstruction device has a correction unit for carrying out an artifact-reduced image reconstruction in the artifact-affected subregions of the examination region, wherein only artifact-reduced subimage data of the artifact-affected subregions is generated. Part of at least one embodiment of the inventive image data reconstruction device is also an image generation unit for generating artifact-reduced image data of the entire examination region by combining at least one part of the reconstructed, uncorrected image data and the artifact-reduced subimage data. The artifact-reduced image data generated is then forwarded to an image display device or an image storage unit, where it is either displayed or stored for further processing or transmission to other units.

An image data reconstruction device, comprising:
an input interface to acquire projection measurement data of an examination region of an examination object; and
a processor, configured to
reconstruct uncorrected image data based upon the projection measurement data,
determine artifact-affected subregions of the examination region based upon uncorrected image data,
carry out an artifact-reduced image reconstruction in the artifact-affected subregions of the examination region, only artifact-reduced subimage data of the artifact-affected subregions being generated, and generate artifact-reduced image data of an entirety of the examination region by combining at least one part of the uncorrected image data and the artifact-reduced subimage data.

At least one embodiment of the inventive computed tomography system has a scanner unit for capturing a region to be examined of an examination object, a control device for controlling the scanner unit and at least one embodiment of the inventive image data reconstruction device.

The components of at least one embodiment of the inventive image data reconstruction device can be configured mainly in the form of software components. This relates in particular to parts of the reconstruction unit, the subregion determination unit, the correction unit and the image generation unit. Fundamentally however, these components can also, in part, be realized in particular, if particularly rapid calculations are involved, in the form of software-supported hardware, for example, FPGAs or the like. Similarly, the required interfaces can be configured, for example, where only an acceptance of data from other software components is concerned, as software interfaces. However, they can also be configured as interfaces constructed from hardware, which are controlled by suitable software.

A realization largely through software has the advantage that computer systems already conventionally used for medical tasks can easily be upgraded with a software update in order to operate as a reconstruction device in the manner according to the invention. In this respect, the object is also achieved via a corresponding computer program product with a computer program which is loadable directly into a storage device of a computer system of this type, having program portions in order to carry out all the steps of the method according to at least one embodiment of the invention when the computer program is executed in the computer system.

At least one embodiment is directed to a computer program product including, apart from the computer program, additional components, if relevant, such as for example, documentation and/or additional components including hardware components, for example, hardware keys (dongles, etc.) in order to use the software.

For transport to the storage device of the computer system and/or for storage at the computer system, a computer-readable medium, for example, a memory stick, a hard disk or another transportable or firmly installed data carrier can be used on which the program portions of the computer program which are readable and executable by a computer unit are stored. For this, the computer unit can have, for example, one or more cooperating microprocessors or the like.

BRIEF DESCRIPTION OF THE DRAWINGS

The invention will be described again in greater detail below using example embodiments by reference to the accompanying drawings. In the drawings.

DETAILED DESCRIPTION OF THE EXAMPLE EMBODIMENTS

Figure 1:
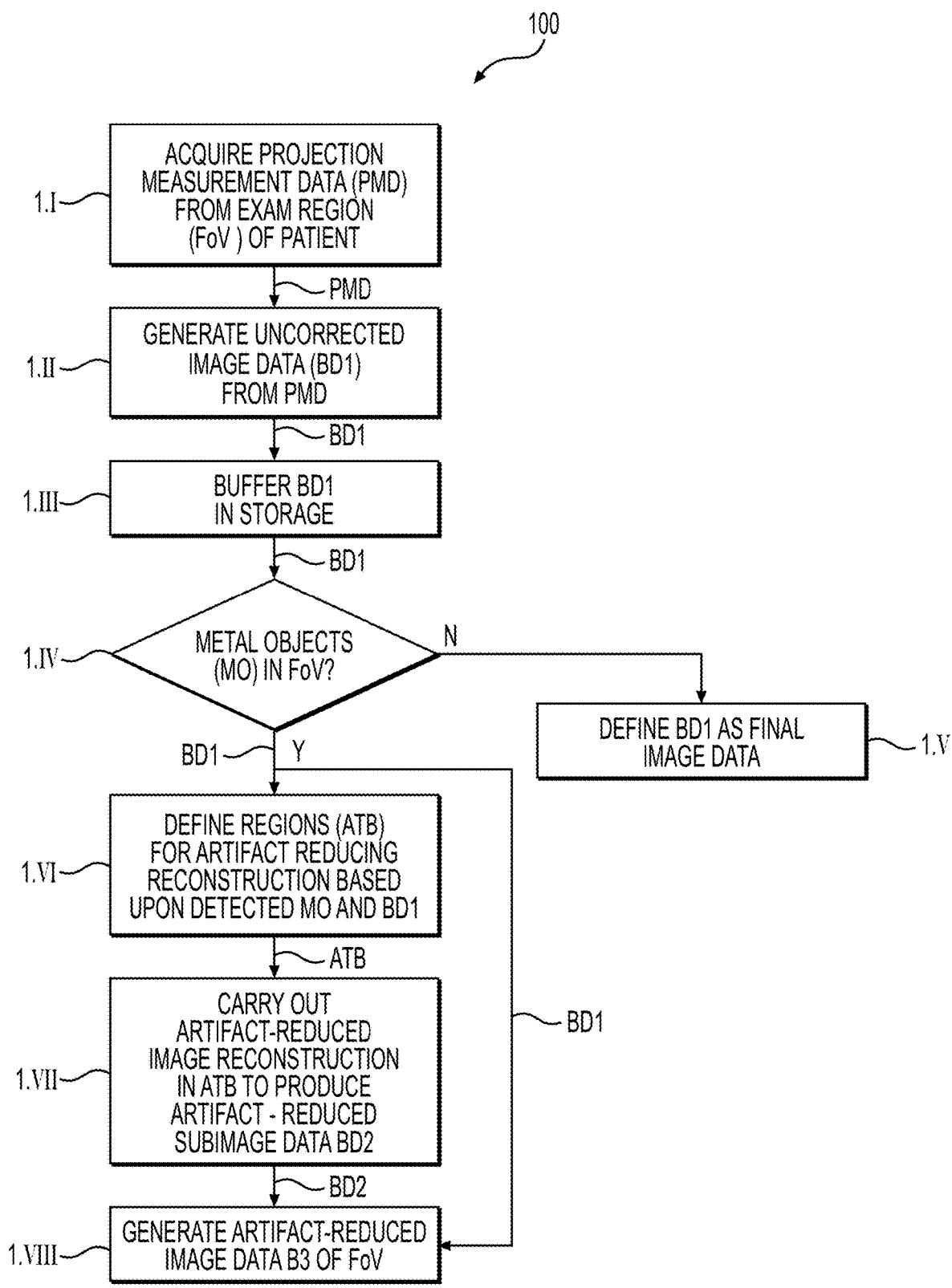
FIG. 1 shows a flow diagram which illustrates an adaptive method for generating CT image data according to an example embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

With at least one embodiment of the inventive adaptive method for generating CT image data, projection measurement data is acquired of an examination region of an examination object. Furthermore, uncorrected image data is generated of the examination region. The examination region may be a body region of a patient, for instance. In the event of a non-medical application, the examination region may however also be part of an inanimate object. The uncorrected image data can be reconstructed for instance on the basis of the projection measurement data, it can however also comprise image data, which is obtained by recording a topogram or by generating RTD data (Real-time Display Data), i.e. real-time image data, sometimes also referred to as raw image data. In general image data of the examination region is to be understood as "uncorrected" image data, which has not yet been subjected to artifact correction and may have image artifacts, for instance metal artifacts.

Artifact-affected subregions of the examination region are then determined on the basis of at least one part of the uncorrected image data. I.e., it is in particular determined whether and possibly in which subregion of the examination region artifacts occur in the uncorrected image data. In other words, the positions of the artifacts and their extent in the examination region are determined and subregions which contain the artifacts are defined. Such a determination of artifacts can take place by way of characteristic properties of the determined image data and projection measurement data, such as, for instance, an attenuation or a density value in a specific region.

Furthermore, an artifact-reduced image reconstruction is carried out in the artifact-affected subregions of the examination region, wherein only artifact-reduced subimage data of the artifact-affected subregions is generated. In the event that artifacts are metal artifacts, artifacts can be corrected, for instance, with the aid of what is known as an iMAR reconstruction method (iMAR—iterative Metal Artifact Reduction). In general, an artifact-reduced image reconstruction is to comprise an image reconstruction method, with which image artifacts can be reduced.

Finally, artifact-reduced image data of the entire examination region is generated by combining at least one part of the uncorrected image data and the artifact-reduced subimage data. The uncorrected image data used for the combination can be, for instance, uncorrected image data, which in the step of generating uncorrected image data of the examination region, has been reconstructed on the basis of the projection measurement data acquired. The determination of the regions or subregions with artifacts is preferably not carried out after, but instead during the reconstruction of uncorrected image data.

In the event that in the step of generating uncorrected image data "provisional" image data, such as for instance topograms or RTD image data, has been generated, i.e. the definition of the subregions with artifacts to be corrected took place on the basis of this "provisional" image data, with the inventive method, uncorrected image data is still reconstructed on the basis of the acquired projection measurement data in addition to the "provisional" image data, wherein at least one part of this reconstructed uncorrected image data is then combined with the artifact-reduced subimage data to form artifact-reduced image data. In particular, the uncorrected image data, which has been reconstructed on the basis of the acquired projection measurement data, is used as image data in the subregions of the examination region, in which no artifacts have been located.

In principle, at least one embodiment of the inventive method can be used independently of the correction algorithm used. It is necessary to locate artifacts or regions, to which an artifact formation is restricted.

Advantageously for some correction methods, the reconstruction of this uncorrected image data can be restricted to regions in which no artifacts have been found, as a result of which the image generation process or image reconstruction process can be made even quicker.

The decision as to whether and in which subregions an artifact correction takes place is preferably made in an automated manner. In this way the user always obtains an optimal data record, without having to have special knowledge in order to be able to locate artifacts. By way of an intelligent selection of the image regions, which require an artifact correction, in particular a metal artifact correction, the image quality can be improved and nevertheless the data quantity to be processed when image data is generated can advantageously be reduced, as a result of which the whole imaging process is made quicker. The method can also be applied to artifacts other than metal artifacts.

One example of a method for correcting motion artifacts is the iTRIM method (intelligent time resolution improvement method). This method improves a time resolution in regions in which motion artifacts are visible. During a thorax imaging, such a method can advantageously be restricted to regions of the heart, in which the motion artifacts are visible.

With the iMAR reconstruction mentioned, it is in any case always useful to generate the uncorrected volume as a reference, since in rare cases the algorithm can also correct inaccurately.

However if correction algorithms other than iMAR are used in the inventive method, in which uncorrected images are not required for the artifact-affected subregions of the examination region, these can be saved, i.e. it is possible to dispense with a reconstruction of uncorrected image data in artifact-affected subregion.

In this case it is sufficient to generate a single data record or image data record on the basis of both supplementary reconstructed image data. With this version or these other correction methods, such as, for instance iTRIM, there is the smallest quantity of image data and the smallest reconstruction outlay, since no image region is reconstructed twice.

At least one embodiment of the inventive image data reconstruction device has an input interface for acquiring projection measurement data of an examination region of an examination object. Part of the inventive image data reconstruction device is also a reconstruction unit for reconstructing uncorrected image data on the basis of the projection measurement data. At least one embodiment of the inventive image data reconstruction device moreover comprises a subregion determination unit for determining artifact-affected subregions of the examination region on the basis of uncorrected image data. Furthermore, at least one embodiment of the inventive image data reconstruction device has a correction unit for carrying out an artifact-reduced image reconstruction in the artifact-affected subregions of the examination region, wherein only artifact-reduced subimage data of the artifact-affected subregions is generated. Part of at least one embodiment of the inventive image data reconstruction device is also an image generation unit for generating artifact-reduced image data of the entire examination region by combining at least one part of the reconstructed, uncorrected image data and the artifact-reduced subimage data. The artifact-reduced image data generated is then forwarded to an image display device or an image storage unit, where it is either displayed or stored for further processing or transmission to other units.

At least one embodiment of the inventive computed tomography system has a scanner unit for capturing a region to be examined of an examination object, a control device for controlling the scanner unit and the inventive image data reconstruction device.

The components of at least one embodiment of the inventive image data reconstruction device can be configured mainly in the form of software components. This relates in particular to parts of the reconstruction unit, the subregion determination unit, the correction unit and the image generation unit. Fundamentally however, these components can also, in part, be realized in particular, if particularly rapid calculations are involved, in the form of software-supported hardware, for example, FPGAs or the like. Similarly, the required interfaces can be configured, for example, where only an acceptance of data from other software components is concerned, as software interfaces. However, they can also be configured as interfaces constructed from hardware, which are controlled by suitable software.

A realization largely through software has the advantage that computer systems already conventionally used for medical tasks can easily be upgraded with a software update in order to operate as a reconstruction device in the manner according to the invention. In this respect, the object is also achieved via a corresponding computer program product with a computer program which is loadable directly into a storage device of a computer system of this type, having program portions in order to carry out all the steps of the method according to at least one embodiment of the invention when the computer program is executed in the computer system.

At least one embodiment is directed to a computer program product including, apart from the computer program, additional components, if relevant, such as for example, documentation and/or additional components including hardware components, for example, hardware keys (dongles, etc.) in order to use the software.

For transport to the storage device of the computer system and/or for storage at the computer system, a computer-readable medium, for example, a memory stick, a hard disk or another transportable or firmly installed data carrier can be used on which the program portions of the computer program which are readable and executable by a computer unit are stored. For this, the computer unit can have, for example, one or more cooperating microprocessors or the like.

The dependent claims and the description below each contain particularly advantageous embodiments and developments of the invention. Here, in particular, the claims of one claim category can also be developed similarly to the dependent claims of another claim category and the description passages belonging thereto. In addition, within the context of embodiments of the invention, the various features of different example embodiments and claims can also be combined to form new example embodiments.

In one embodiment of the inventive, adaptive method for generating CT image data, only the uncorrected image data from artifact-free subregions is used in order to generate the artifact-reduced image data. Advantageously the uncorrected image data is employed for subregions of the overall image, in which no artifacts occur. Consequently, an optimal image quality is reached for these regions, without generating additional data for these image regions in an artifact correction method. The artifact correction is then restricted to the artifact-affected regions. In this way an optimal image quality is also achieved in the artifact-affected regions.

Since the uncorrected image data in the artifact-affected image regions can negatively affect the image quality, it is advantageous not to use the uncorrected image data for these image regions, as a result of which the image quality of the overall image is improved.

In a preferred embodiment of the inventive, adaptive method for generating CT image data, when artifact-affected subregions are determined, it is determined whether metal objects are situated in the examination region and it is determined in which subregions of the examination region the metal objects are situated. Metal objects can be located in the respective imaging region particularly by the material density. Metal artifact-affected regions or subregions, which preferably occur at the position of these metal objects and therearound, can advantageously be determined by locating the metal objects.

In a particularly preferred embodiment of the inventive, adaptive method for generating CT image data, potential subregions, which may be artifact-affected, are determined in advance via real-time image data and/or topogram image data. If artifact-affected subregions are possibly located via real-time image data and/or topogram image data, then the actual artifact-affected subregions are then additionally also determined on the basis of the uncorrected image data, which is reconstructed on the basis of the acquired projection measurement data and which is assigned to the potential subregions determined. Advantageously the regions of the reconstructed image data, in which artifacts are sought, can be localized via the real-time image data and/or topogram image data.

Furthermore, a decision can be made on the basis of the real-time image data and/or topogram image data to determine whether artifacts actually exist and whether the uncorrected image data has to be searched for artifacts and has to be buffered in order to generate artifact-corrected image data or can be forwarded directly to an image storage device or a display unit on account of missing artifacts. Real-time image data is also to be understood as the raw image data also referred to as real-time display data (RTD data). By this procedure, the effort involved in buffering image data can be reduced and the process speed increased.

In a particularly usefully applicable variant of at least one embodiment of the inventive, adaptive method for generating CT image data, the real-time image data is consequently used for a decision to determine to whether or not an artifact-affected reconstruction is to be performed.

In one variant of at least one embodiment of the inventive, adaptive method for generating CT image data, a topogram of the examination region is recorded and potential subregions, which could be artifact-affected, are determined in advance via the topogram. A low resolution overview image carried out prior to the actual image recording, typically an x-ray image recording, of the examination region, is to be understood in this context as a topogram. If no real-time image data is present, for instance, the decision as to whether an artifact correction is actually to take place can also be made via the topogram. In this way the entire image recording method can be made quicker.

In one embodiment of the inventive, adaptive method for generating CT image data, after its reconstruction the uncorrected image data is buffered for the generation of artifact-reduced image data only in the event, for instance in a cache storage device, that it has been determined in advance that an artifact reduction actually has to be carried out. In this way the data processing and buffering of image data can be restricted to the requisite degree so that the process is made quicker.

Preferably with the internal data transmission between the image data reconstruction device used to reconstruct the artifact-reduced image data and an image display device used for image display, only one data record, which comprises the artifact-reduced image data, is transmitted per image display. In other words, only the corrected image data is forwarded to the image display in order to restrict the data traffic to the most necessary. The speed of the imaging method is advantageously increased in this way.

FIG. 1 shows a flow diagram 100 which illustrates an adaptive method for generating artifact-reduced CT image data according to an example embodiment of the invention. In the step 1.I, projection measurement data PMD is firstly acquired of an examination region FoV of a patient with the aid of a scanner unit of a computed tomography system. In step 1.II, uncorrected image data BD1, which is still not artifact-reduced, is further reconstructed on the basis of the projection measurement data PMD. A reconstruction method based on the filtered back projection can be used as a reconstruction method, for instance. In step 1.III, the uncorrected reconstructed image data BD1 is buffered and retained for a subsequent generation of artifact-reduced image data BD3. The buffering can take place in a storage unit ZS of the computed tomography system which is embodied as a cache.

In the step 1.IV, an evaluation of the buffered, uncorrected image data BD1 can then be performed, to determine whether metal objects MO can be found in the examination region FoV. In the event in step 1.IV that no metal objects MO could be found in the examination region FoV, which is identified in FIG. 1 with "n", step 1.V then proceeds. In step 1.V, the reconstructed uncorrected image data BD1 is defined as final image data BD3 and output to a display unit for further processing or assessment. In the event that metal objects MO have been found in the step 1.IV, which is identified in FIG. 1 with "y", step 1.VI then proceeds.

In step 1.VI, regions ATB, in which an artifact-reducing reconstruction is subsequently to be used, are defined on the basis of the detected metal objects MO and their position. This step can be carried out, for instance, as a function of a determined density, i.e. material density, at a respective position in the examination region FoV. Very dense regions indicate the presence of metal objects MO. This determining step can preferably take place automatically on the basis of the determined image data BD1. Finally, in step 1.VII, an artifact-reduced image reconstruction is carried out in the metal artifact-affected subregions ATB of the examination region FoV. I.e. the artifact-reducing image reconstruction takes place on the basis of projection measurement data PMD (ATB), which forms a sub quantity of the projection measurement data PMD acquired in step 1.I and subregions ATB of the examination region FoV are assigned to the determined metal artifact-affected subregions ATB. Therefore, only artifact-reduced subimage data BD2 of the metal artifact-affected subregions ATB is generated. Finally artifact-reduced image data BD3 of the overall examination region FoV is generated in step 1.VIII by combining the uncorrected image data BD1 and the artifact-reduced subimage data BD2. In other words, an image data record is generated, in which conventional image data BD1 is used for the non-metal artifact-affected regions of the examination region and artifact-reduced subimage data BD2 is used only in the metal artifact-affected regions ATB.

Figure 2:
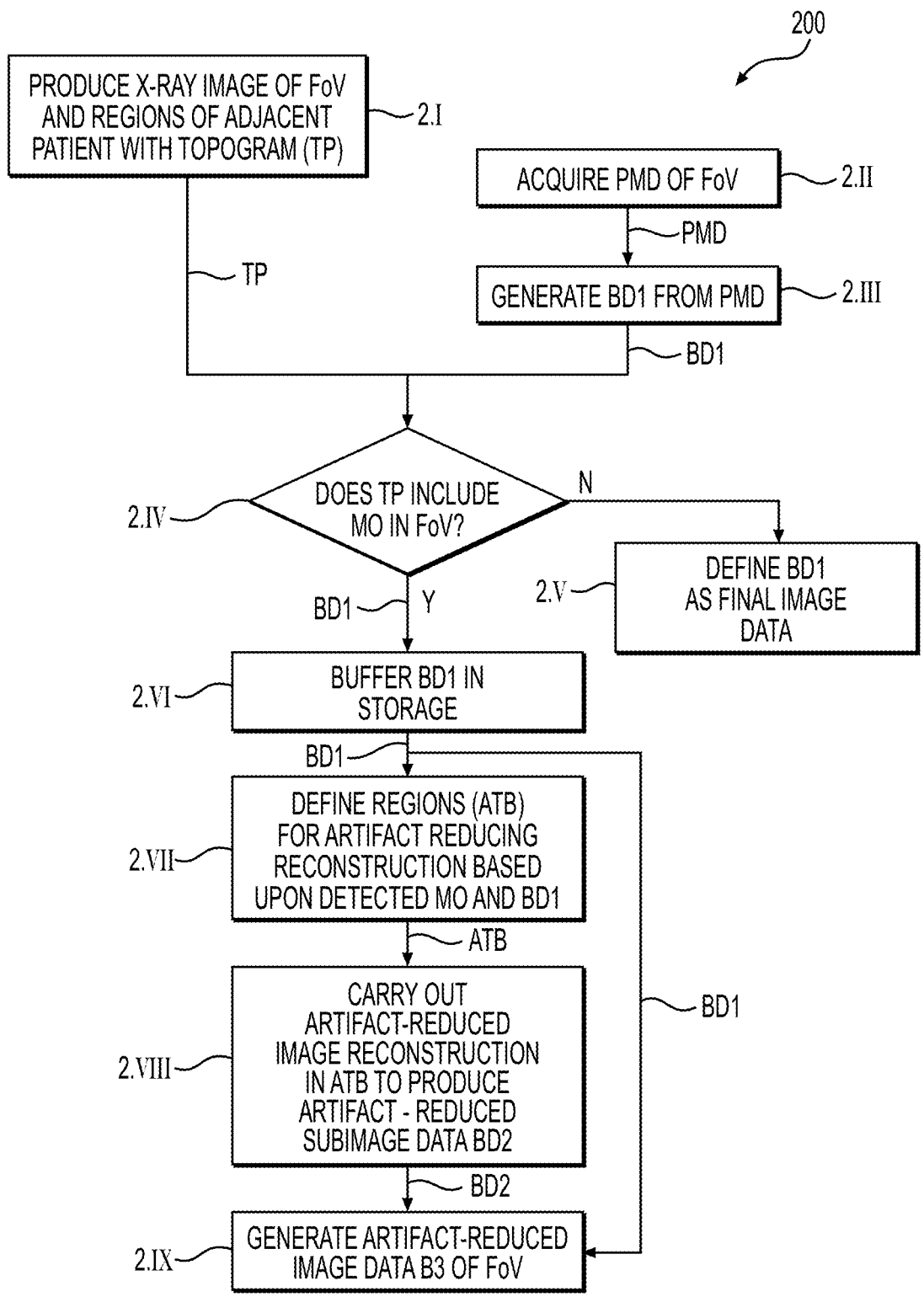
FIG. 2 shows a flow diagram which illustrates an adaptive method for generating CT image data according to a second example embodiment of the invention.

FIG. 2 shows a flow diagram 200 which illustrates an adaptive method for generating artifact-reduced CT image data BD3 according to a second example embodiment of the invention.

In step 2.I, an x-ray image of an examination region FoV and also regions of a patient adjacent thereto, both with minimal resolution, is initially performed with the aid of a topogram TP. In step 2.II, projection measurement data PMD of an examination region FoV is then acquired with the aid of a scanner unit of a computed tomography system. In step 2.III, first image data BD1 which is still not artifact-reduced is also reconstructed on the basis of the projection measurement data PMD.

In step 2.IV, the topogram TP is then evaluated to determine whether metal objects MO are found in the examination region FoV or possibly also in regions adjacent thereto. In the event, in step 2.IV, that no metal objects MO could be found in the examination region FoV or possibly also in regions adjacent thereto, which is identified in FIG. 2 with "n", step 2.V proceeds. In step 2.V, the reconstructed, uncorrected image data BD1 is defined as final image data BD3 and output to a display unit for further processing or assessment. In the event that in step 2.IV metal objects MO have been found, which is identified in FIG. 2 with "y", step 2.VI then proceeds, in which the reconstructed, uncorrected image data BD1 is buffered and retained for a subsequent generation of artifact-reduced image data BD3.

The remaining steps 2.VII to 2.IX then correspond to the steps 1.VI to 1.VIII illustrated in FIG. 1 and are not displayed again in detail at this point.

Figure 3:
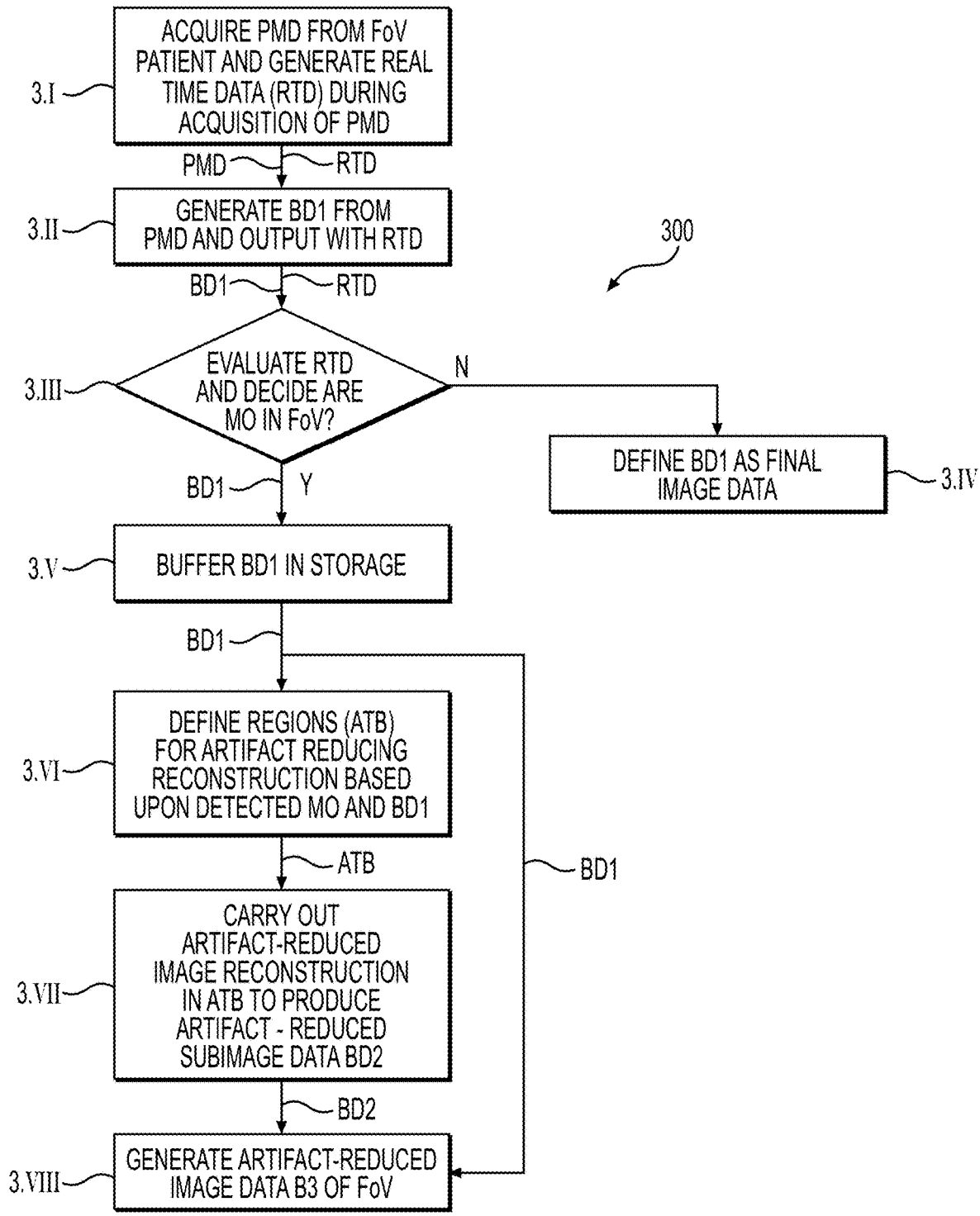
FIG. 3 shows a flow diagram which illustrates an adaptive method for generating CT image data according to a third example embodiment of the invention.

FIG. 3 is a flow diagram 300 which illustrates an adaptive method for generating artifact-reduced CT image data according to an example embodiment of the invention. In step 3.I, projection measurement data PMD is firstly acquired with the aid of a scanner unit of a computed tomography system. In addition, with this example embodiment, what is known as real-time image data RTD is generated on the basis of the respective already currently acquired projection measurement data, which represents low resolution image data, which is reconstructed during the acquisition of the projection measurement data PMD. In step 3.II, first image data BD1, which is still not artifact-reduced, is reconstructed on the basis of the projection measurement data PMD.

In the further course of the method, in step 3.III, an evaluation of the real-time image data RTD is then performed to determine whether metal objects MO can be found in the examination region FoV. In the event, in step 3.III, that no metal objects MO could be found in the examination region FoV, which is identified in FIG. 1 with "n", step 3.IV then proceeds. In step 3.IV, the reconstructed first image data BD1 is defined as final image data BD3 and output to a display unit for further processing or assessment. In the event, in step 3.III, that metal objects MO have been found, which is identified in FIG. 1 with "y", step 3.V then proceeds, in which the uncorrected, reconstructed image data BD1 is buffered and retained for a subsequent generation of artifact-reduced image data BD3. The buffering can take place in a storage unit embodied as a cache or a corresponding storage area of a storage unit.

The remaining steps 3.VI to 3.VIII then correspond to the steps 1.VI to 1.VIII illustrated in FIG. 1 and are not displayed again in detail at this point.

Figure 4:
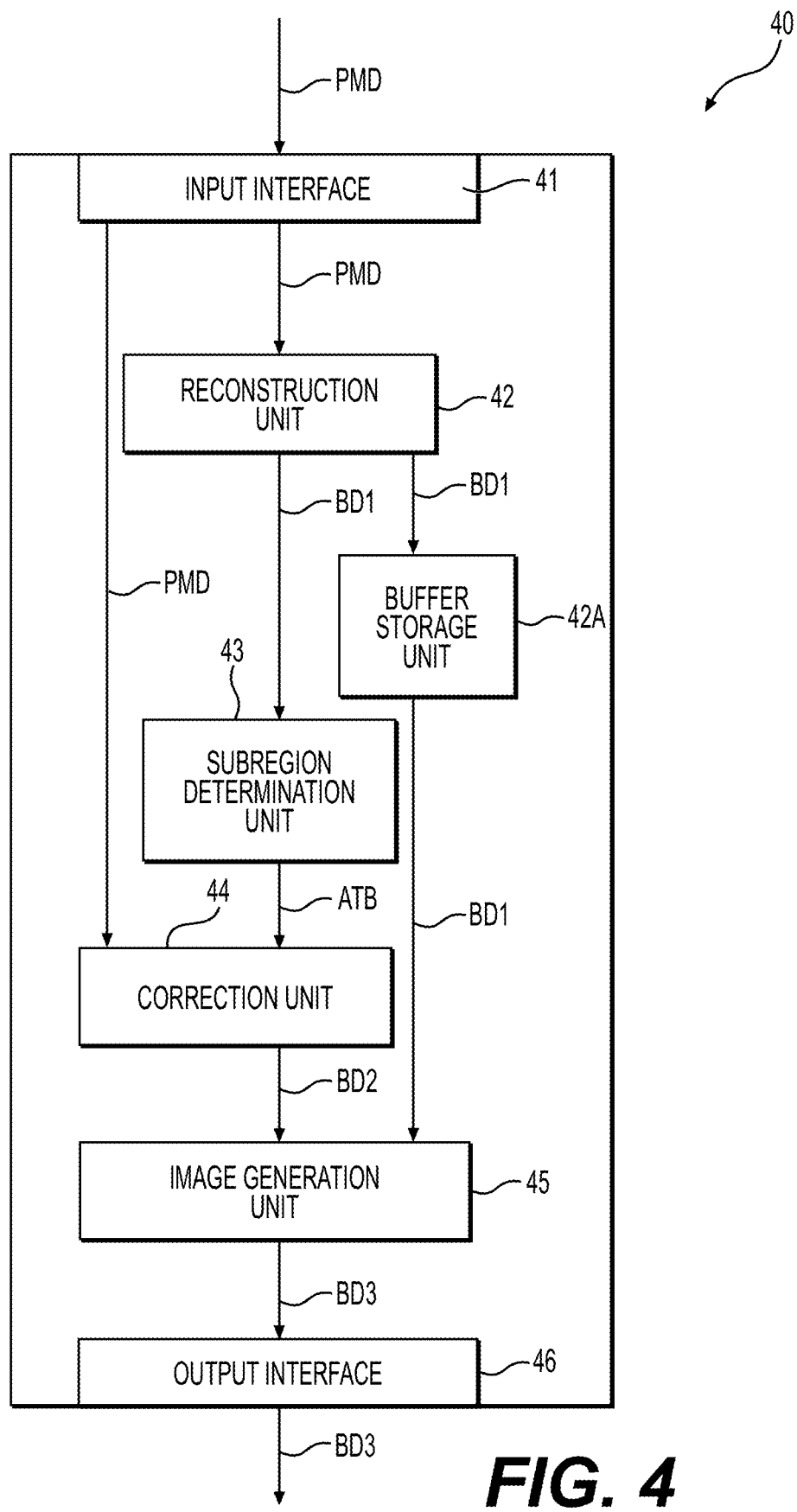
FIG. 4 shows a block diagram, with which an image data reconstruction device according to an example embodiment of the invention is shown.

An image data reconstruction device 40 according to an example embodiment of the invention is shown schematically in FIG. 4. The image data reconstruction device 40 has an input interface 41, which receives projection measurement data PMD of an examination region FoV of an examination object O from a scanner unit of a CT system (see FIG. 5). The projection measurement data PMD is forwarded to a reconstruction unit 42, which is set up to reconstruct first uncorrected image BD1 on the basis of the projection measurement data PMD. The reconstructed image data BD1 is then buffered in a buffer storage unit 42a, also referred to as cache.

Part of the image data reconstruction device 40 is also a subregion determination unit 43, which is set up to determine metal artifact-affected subregions ATB of the examination region FoV on the basis of the uncorrected image data BD1. The information relating to the metal artifact-affected subregions ATB and the projection measurement data PMD is transmitted to a correction unit 44, which is set up to carry out an artifact-reduced image reconstruction, for instance with the aid of the already cited iMAR artifact correction method, in the metal artifact-affected subregions ATB of the examination region FoV. In such cases the projection measurement data PMD assigned to the metal artifact-affected subregions ATB is used for an artifact-reduced reconstruction of artifact-reduced subimage data BD2, wherein only artifact-reduced subimage data BD2 of the metal artifact-affected subregions ATB is generated. The artifact-reduced subimage data BD2 and complementary buffered uncorrected image data BD1 is transmitted to an image generation unit 45, which generates artifact-reduced image data BD2 of the overall examination region FoV. In such cases the artifact-reduced subimage data BD2 and the complementary uncorrected image data BD1, i.e. the image data BD1, which has been received in the artifact-free subregions of the examination region, are combined. The generated artifact-reduced image data BD3 is then output via an output interface 46 to a data storage unit or an image display unit (see FIG. 5).

Figure 5:
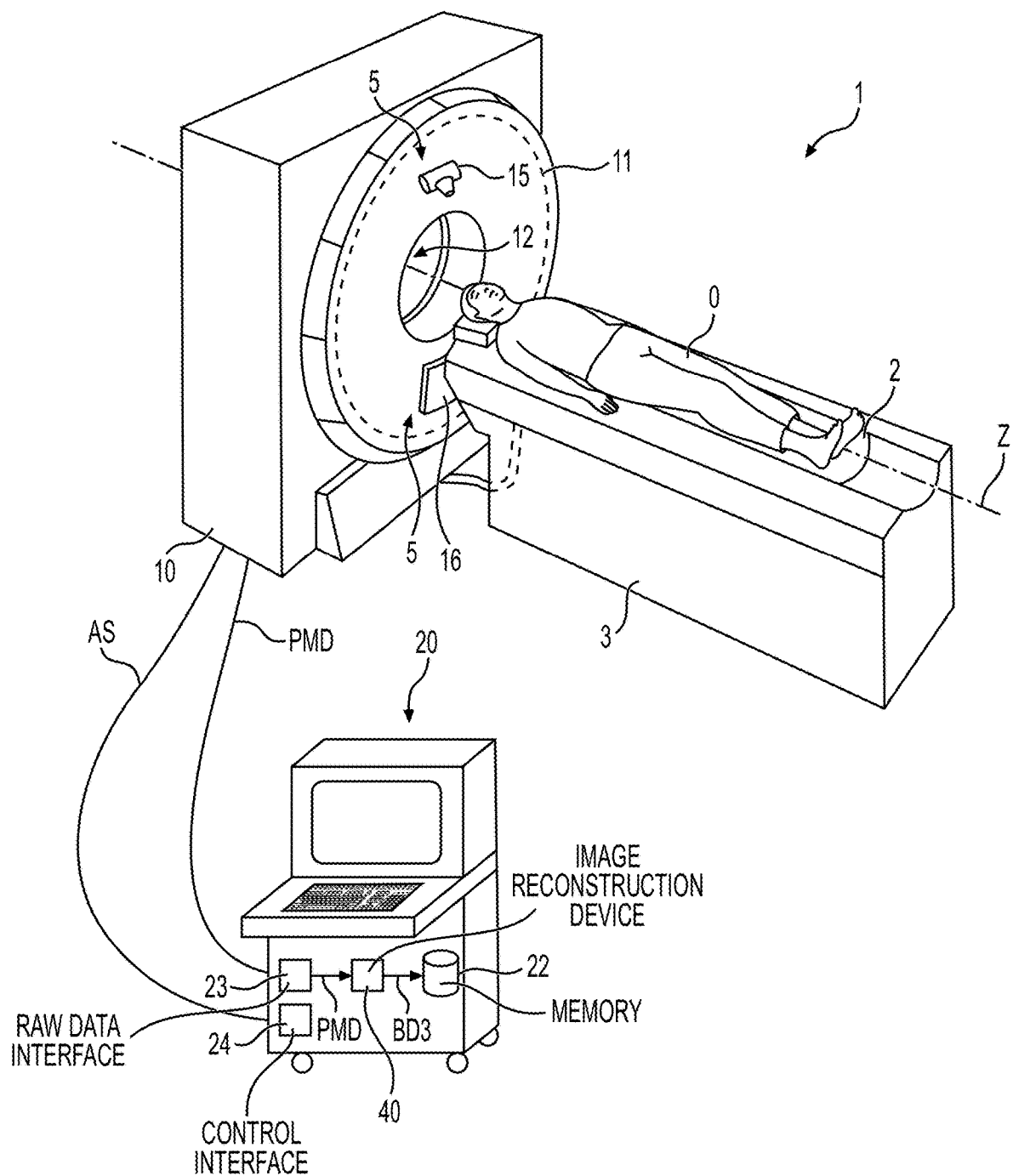
FIG. 5 shows a schematic representation of a computed tomography system according to one example embodiment of the invention.

FIG. 5 illustrates a schematic representation of a computed tomography system 1 according to an example embodiment of the invention. The computed tomography system 1 comprises the image data reconstruction device 40 illustrated in FIG. 4, which is part of a control device 20 of the computed tomography system. The CT system 1 consists otherwise essentially of a typical scanner unit 10 in which arranged on a gantry 11 a projection data acquisition unit 5 with a detector 16 and an X-ray source 15 arranged opposite the detector 16 revolves around a scanning space 12. Situated in front of the scanner unit 10 is a patient positioning device 3 or patient couch 3, the upper part 2 of which with a patient O situated thereon can be displaced relative to the scanner unit 10 in order to move the patient O through the scanning space 12 relative to the detector system 16. The scanner unit 10 and the patient couch 3 are controlled by the control device 20, already mentioned, from which acquisition control signals AS are transmitted via a conventional control interface 24 in order to control the whole system in the conventional manner according to pre-determined measurement protocols.

In the event of a spiral acquisition, due to a movement of the patient O along the z-direction, which corresponds to the system axis z through the scanning space 12 and the simultaneous circulation of the x-ray source 15, a helical path results for the x-ray source 15 relative to the patient P during the scan. The detector 16 always runs in parallel with and opposite to the x-ray source 15 in order to capture projection measurement data PMD which then is used for reconstructing volume image data and/or slice image data. Similarly, a sequential scanning method can also be carried out, wherein a fixed position in the z-direction is approached and then, during a rotation, a partial rotation or a plurality of rotations at the z-position in question, the required projection measurement data PMD is captured in order to reconstruct a sectional image at this z-position or in order to reconstruct image data from the projection data of a plurality of z-positions. The method according to the invention can, in principle, also be used in other CT systems, for example, with a plurality of x-ray sources and/or detectors and/or with a detector forming a complete ring. For example, the inventive method can also be used on a system with a stationary patient couch and a gantry moving in the z-direction (known as a sliding gantry).

The projection measurement data PMD (also known as raw data) acquired by the detector 16 is transferred via a raw data interface 23 to the control device 20. This raw data PMD is then further processed, possibly following a suitable pre-processing (e.g. filtration and/or radiation hardening correction), in an image data reconstruction device 40 according to the invention, which in this example embodiment is realized in the control device 20 in the form of software on a processor. This image data reconstruction device 40 reconstructs artifact-reduced image data BD3, on the basis of the raw data PMD, with the aid of the inventive method illustrated in FIG. 1 to FIG. 3.

The image data BD3 determined by the reconstruction device 40 is then stored in a memory 22 of the control device 20 and/or output conventionally on the monitor of the control device 20. Via an interface (not shown in FIG. 5), they can also be fed into a network connected to the computed tomography system 1, for example, a radiological information system (RIS), and stored in a mass memory store accessible there or output as images to printers or filming stations connected there. The data can thus be further processed in any desired manner and then stored or output.

The components of the image reconstruction device 40 can be realized mainly or completely in the form of software elements on a suitable processor. In particular, the interfaces can also be configured purely as software between these components. It is required only that access possibilities exist in suitable memory regions in which the data can be suitably placed in intermediate storage and called up again and updated at any time.

Finally, it should again be noted that the methods and devices described above are merely preferred example embodiments of the invention and that the invention can also be varied by a person skilled in the art without departing from the scope of the invention as defined by the claims. Therefore the described methods and devices can be used not only for the medical imaging, but they can instead also be used for other, non-medical purposes. For the sake of completeness, it should also be mentioned that the use of the indefinite article "a" or "an" does not preclude the relevant features from also being present plurally. Similarly, the expression "unit" does not preclude this consisting of a plurality of components which can possibly also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An adaptive method for generating CT image data, comprising:
   acquiring projection measurement data of an examination region of an examination object;
   generating uncorrected image data of the examination region;
   determining artifact-affected subregions of the examination region based upon at least one part of the uncorrected image data;
   carrying out an artifact-reduced image reconstruction in the artifact-affected subregions of the examination region, only artifact-reduced subimage data of the artifact-affected subregions being generated; and
   generating artifact-reduced image data of an entirety of the examination region by combining at least one part of the uncorrected image data and the artifact-reduced subimage data,
   wherein the uncorrected image data includes at least one of topogram image data and real-time image data,
   wherein at least one of the real-time image data and the topogram image data is used in determining whether or not to perform an artifact-affected reconstruction, and
   wherein, after reconstruction for the generating of the artifact-reduced image data, reconstructed, uncorrected image data is buffered only in an event of a determination that an artifact reduction has to be carried out.

2. The method of claim 1, wherein in the generating of the uncorrected image data, uncorrected image data is reconstructed based upon the projection measurement data acquired and at least one part of the reconstructed, uncorrected image data is combined with the artifact-reduced subimage data in the generating of the artifact-reduced image data.

3. The method of claim 2, wherein the uncorrected image data includes at least one of topogram image data and real-time image data.

4. The method of claim 2, wherein, in generating the artifact-reduced image data, only the uncorrected image data from artifact-free subregions is used.

5. The method of claim 1, wherein, in generating the artifact-reduced image data, only the uncorrected image data from artifact-free subregions is used.

6. The method of claim 5, wherein the uncorrected image data includes at least one of topogram image data and real-time image data and wherein the artifact-affected subregions are determined based upon at least one of the real-time image data and the topogram image data.

7. The method of claim 5, wherein the uncorrected image data includes at least one of topogram image data and real-time image data and wherein potential subregions, which may be artifact-affected, are determined in advance via at least one of the real-time image data and the topogram image data and wherein artifact-affected subregions are determined based upon reconstructed, uncorrected image data, assigned to the potential subregions determined.

8. The method of claim 5, wherein the uncorrected image data includes at least one of topogram image data and real-time image data and wherein at least one of the real-time image data and the topogram image data is used in determining whether or not to perform an artifact-affected reconstruction.

9. The method of claim 1, wherein the determining of the artifact-affected subregions includes:
   determining whether metal objects are located in the examination region, and
   determining the artifact-affected subregions of the examination region in which the metal objects are located.

10. The method of claim 9, wherein the uncorrected image data includes at least one of topogram image data and real-time image data and wherein the artifact-affected subregions are determined based upon at least one of the real-time image data and the topogram image data.

11. The method of claim 9, wherein the uncorrected image data includes at least one of topogram image data and real-time image data, wherein potential subregions, which may be artifact-affected, are determined in advance via at least one of the real-time image data and the topogram image data and wherein artifact-affected subregions are determined based upon reconstructed, uncorrected image data, assigned to the potential subregions determined.

12. The method of claim 9, wherein the uncorrected image data includes at least one of topogram image data and real-time image data and wherein at least one of the real-time image data and the topogram image data is used in determining whether or not to perform an artifact-affected reconstruction.

13. The method of claim 1, wherein the artifact-affected subregions are determined based upon at least one of the real-time image data and the topogram image data.

14. The method of claim 1, wherein potential subregions, which may be artifact-affected, are determined in advance via at least one of the real-time image data and the topogram image data and wherein artifact-affected subregions are determined based upon reconstructed, uncorrected image data, assigned to the potential subregions determined.

15. The method of claim 1, wherein with an internal data transmission between an image data reconstruction device used to reconstruct the artifact-reduced image data and an image display device per image display, only one data record, including the artifact-reduced image data, is transmitted.

16. A non-transitory memory storing a computer program, directly loadable into a computing unit of a computed tomography system, including program portions to carry out the method of claim 1 when the computer program is executed in the computing unit.

17. A non-transitory computer-readable medium storing executable program portions, configured to be executable by a computer unit to carry out the method of claim 1 when the program portions are executed by the computer unit.

18. The method of claim 1, wherein, in generating the artifact-reduced image data, only the uncorrected image data from artifact-free subregions is used.

19. An image data reconstruction device, comprising:
an input interface to acquire projection measurement data of an examination region of an examination object;
a reconstruction unit to reconstruct uncorrected image data based upon the projection measurement data;
a subregion determination unit to determine artifact-affected subregions of the examination region based upon uncorrected image data;
a correction unit to carry out an artifact-reduced image reconstruction in the artifact-affected subregions of the examination region, only artifact-reduced subimage data of the artifact-affected subregions being generated; and
an image generation unit to generate artifact-reduced image data of an entirety of the examination region by combining at least one part of the uncorrected image data and the artifact-reduced subimage data,
wherein the uncorrected image data includes at least one of topogram image data and real-time image data, used in determining whether or not to perform an artifact-affected reconstruction and wherein, after reconstruction to generate the artifact-reduced image data, uncorrected image data is buffered only after a determination that artifact reduction is necessary.

20. A computed tomography system, comprising:
a scanner unit to capture a region, to be examined, of an examination object;
a control device to control the scanner unit; and
the image data reconstruction device of claim 19.

21. An image data reconstruction device, comprising:
an input interface to acquire projection measurement data of an examination region of an examination object; and
a processor, configured to
reconstruct uncorrected image data based upon the projection measurement data,
determine artifact-affected subregions of the examination region based upon uncorrected image data,
carry out an artifact-reduced image reconstruction in the artifact-affected subregions of the examination region, only artifact-reduced subimage data of the artifact-affected subregions being generated, and
generate artifact-reduced image data of an entirety of the examination region by combining at least one part of the uncorrected image data and the artifact-reduced subimage data,
wherein the uncorrected image data includes at least one of topogram image data and real-time image data, used in determining whether or not to perform an artifact-affected reconstruction and wherein, after reconstruction to generate the artifact-reduced image data, uncorrected image data is buffered only after a determination that artifact reduction is necessary.

22. A computed tomography system, comprising:
an x-ray scanner to capture a region, to be examined, of an examination object;
a controller to control the x-ray scanner; and
the image data reconstruction device of claim 21.

* * * * *